United States Patent
Schmidt et al.

(10) Patent No.: US 7,477,374 B2
(45) Date of Patent: Jan. 13, 2009

(54) METHOD AND DEVICE FOR EXAMINING A SEALING SURFACE OF A CONTAINER MOUTH

(75) Inventors: Peter Schmidt, Auetal (DE); Hartwin Stüwe, Obernkirchen (DE)

(73) Assignee: Heye International GmbH, Obernkirchen (DE)

( * ) Notice: Subject to any disclaimer, the term of this patent is extended or adjusted under 35 U.S.C. 154(b) by 236 days.

(21) Appl. No.: 11/329,985

(22) Filed: Jan. 11, 2006

(65) Prior Publication Data

US 2006/0162472 A1  Jul. 27, 2006

(30) Foreign Application Priority Data

Jan. 13, 2005  (DE) ................... 10 2005 001 810

(51) Int. Cl.
*G01N 21/00* (2006.01)
(52) U.S. Cl. ............... 356/239.4; 356/239.5; 250/223 B
(58) Field of Classification Search ... 356/239.1–239.8, 356/240.1, 237.1–237.3; 250/559.45, 223 B, 250/231.14; 209/523, 526
See application file for complete search history.

(56) References Cited

U.S. PATENT DOCUMENTS

| | | | |
|---|---|---|---|
| 2,868,061 A | | 1/1959 | Fedorchak et al. |
| 3,631,255 A | * | 12/1971 | Gender et al. ............ 250/223 B |
| 4,025,201 A | * | 5/1977 | Deane ..................... 356/239.4 |
| 4,498,003 A | | 2/1985 | Cibis |
| 4,610,542 A | * | 9/1986 | Ringlien ................. 356/239.4 |
| 4,731,649 A | | 3/1988 | Chang et al. |
| 5,072,107 A | * | 12/1991 | Apter ..................... 250/223 B |
| 5,661,296 A | * | 8/1997 | Ishizuka et al. ........ 250/231.14 |
| 5,699,152 A | * | 12/1997 | Fedor et al. ............. 356/240.1 |
| 5,905,595 A | * | 5/1999 | Minami ................... 359/618 |
| 6,072,575 A | * | 6/2000 | Loll ........................ 356/239.4 |
| 6,654,116 B1 | * | 11/2003 | Kwirandt ................. 356/240.1 |
| 6,855,901 B1 | * | 2/2005 | Guenard et al. ........... 209/577 |

FOREIGN PATENT DOCUMENTS

| | | |
|---|---|---|
| DE | 2916361 A1 | 11/1980 |
| DE | 3147086 A1 | 7/1983 |
| DE | 3940693 C1 | 5/1991 |
| DE | 3518653 C2 | 7/1991 |
| DE | 3686847 T2 | 2/1993 |

(Continued)

OTHER PUBLICATIONS

European Search Report dated Apr. 26, 2006 for EP 05 02 8619 with an Opinion.

*Primary Examiner*—Sang Nguyen
(74) *Attorney, Agent, or Firm*—Fox Rothschild LLP

(57) ABSTRACT

The invention concerns a method and a device for examining a container mouth for defects in a mouth sealing surface. A light source emits light beams having a direction component impinging tangentially upon the sealing surface. The tangential light beams are scattered as they impinge upon a defect in the sealing surface. At least some of these scattered light beams are detected by a sensor. The tangential direction component is produced by an optical deflecting element disposed between the light source and the mouth. The optical deflecting element is transparent at least to light of certain wavelengths and deflects impinging light beams accordingly. The invention renders it possible to amplify contrasts between defects and other reflections from the sealing surface during the detection of defects in the sealing surface.

22 Claims, 5 Drawing Sheets

FOREIGN PATENT DOCUMENTS

| | | |
|---|---|---|
| DE | 19920007 C1 | 7/2000 |
| EP | 0047936 A1 | 3/1982 |
| EP | 0 657 732 A1 | 10/1994 |
| JP | 02093347 A | 4/1990 |
| WO | WO 90/04773 | 5/1990 |
| WO | WO98/19150 A | 5/1998 |

* cited by examiner (State of the art)

(State of the art)

US 7,477,374 B2

METHOD AND DEVICE FOR EXAMINING A SEALING SURFACE OF A CONTAINER MOUTH

FIELD OF THE INVENTION

The invention relates to a method and a device for detecting defects in the sealing surface of a mouth of a container.

In particular, the container can be a glass bottle or a wide-necked glass. In particular, the mouth can be a mouth for closing the container by means of a crown cork or a screw mouth.

BACKGROUND OF THE INVENTION

During the production of glass bottles, a series of defects can be produced in the sealing surface of the bottle mouth. In order to ensure that the sealing surface can cooperate in a problem-free manner with the closure element provided and in particular leakages are obviated, it is important to detect wrinkles extending e.g. radially over the mouth surface and to separate out the corresponding containers. Other possible flaws in the sealing surface include nicks, orange peel or even other defects. Cracks in the sealing region of a drinks bottle can be the starting point of localized breakage of the mouth lip and thus represent a risk for a consumer drinking from the bottle.

It is known to detect defects in the sealing surface by virtue of the fact that light is transmitted on to the sealing surface and a camera serves to detect light which is diffusely scattered by flaws in the sealing surface. A testing device which is known in practice is illustrated in FIG. 1. The known testing device is designated by the reference numeral 1. Located below the testing device 1 is a glass bottle 2 which is shown only partially and in which a sealing surface 3 of a mouth 4 is examined by means of the testing device 1.

The testing device 1 comprises a light source 5 which emits light beams 9 perpendicularly or almost perpendicularly on to a diffuser disc 10. The diffuser disc 10 comprises an orifice 11 in the center.

A diffuse reflector 13 is disposed below the diffuser disc 10. The reflector 13 is positioned in the shape of a collar around the mouth 4 and comprises a reflective inner surface 14. The reflector 13 comprises a lower orifice 15, below which the mouth 4 is positioned. The reflector 13 can be produced e.g. from iron and can comprise on the inner surface 14 a white color layer to reflect the light. A camera 18 operating as a sensor is disposed above the orifice 11 of the diffuser disc 10 symmetrically with respect to a longitudinal axis 16 of the mouth 4. A housing of the testing device 1 is not shown in FIG. 1. The light which is emitted by the light source 5 on to the diffuser disc 10 consists not only of parallel light beams 9 but also of light beams, not illustrated, which do not impinge perpendicularly upon the diffuser disc 10. The light source 5 can comprise e.g. a series of light-emitting diodes, not illustrated, which have a reflected beam opening angle of 30 to 40°. By virtue of the diffuser disc 10, the impinging light becomes diffuse, i.e. is scattered in all directions. By way of example, two scattered light beams 21 and 22 are illustrated. Further scattered light beams are illustrated in rudimentary fashion at 23. The light beam 21 impinges upon the reflector 13 in parallel with the mouth longitudinal axis 16. In turn, the light according to light beam 21 is scattered by the reflector in all possible directions, as illustrated by the light beam 24 and at 25 by rudimentary light beams.

The light beam 24 passes through the orifice 15 of the reflector 13 on to the sealing surface 3. Since the sealing surface 3 is smooth, the light beam 24 is reflected at an angle corresponding to the inclination of the glass surface. The resulting reflected light beam is designated by the reference numeral 26. The reflected light beam 26 also results from a scattering of the light beam 22 which, without previously impinging upon the reflector 13, passes on to the sealing surface 3 where it is also reflected. The two light beams 24 and 22 impinge close to one another but not exactly at the same site upon the sealing surface 3. Since the sealing surface 3 has a strong curvature in the region, both beams are reflected in beams which lie very closely next to one another, and only a resulting light beam, namely the light beam 26, is illustrated in a simplified manner. In this manner, light passes in an annular manner into the camera 18, whereby a so-called reflection ring 28 is produced, as shown in FIG. 2 which schematically illustrates a section of an image 31 recorded by the camera 18. For the sake of completeness, it should be mentioned that some of the light which impinges upon the sealing surface 3 is broken and enters into the glass of the mouth 4.

A further reflection ring 29 is produced by corresponding reflection of light beams at an inner edge 30 of the mouth 4. Since the inner edge 30 has a very much stronger curvature, not illustrated, than the outer edge 27, the inner reflection ring 29 is narrower than the outer reflection ring 28. For the sake of clarity, FIG. 1 does not illustrate light beams which produce the reflection ring 29.

Although light which impinges between the outer edge 27 and the inner edge 30 upon the sealing surface 3 is reflected in a particular direction, it does not impinge upon the camera 18. Therefore, in the camera image 31 this region normally appears dark. At defective points on the sealing surface 3, such as wrinkles, nicks, orange peel or similar deflects, impinging light is diffusely scattered. By reason of this diffuse scattering, light is also scattered into the camera 18 by these defects. By way of example, FIG. 2 illustrates the case where a wrinkle extends approximately in the radial direction over the sealing surface 3. The wrinkle serves to produce in the camera image 31a corresponding bright line 33 which extends between the two reflection rings 28, 29.

A problem which arises in practical usage resides in the fact that the intensity of the reflection rings 28, 29 is generally considerably greater than the intensity of the light 33 which passes into the camera 18 by reason of a defect in the sealing surface 3. The defect image 33 becomes superimposed by virtue of the reflection rings 28, 29, thus making it more difficult to detect defects in the sealing surface 3.

DE 35 18 653 C2 discloses a generic method and a generic device respectively. In order to examine the bottle mouths for defects, interfering reflections of flawless regions of the mouth are obviated by virtue of the fact that specific mouth regions are shielded from a light source. For example, this relates to an upper mouth region (see FIG. 4A). A disadvantage of this shield is that defects cannot be detected in the shielded mouth regions. Furthermore, it is also disclosed in the named document to utilize a shield in order to ensure that light beams which have a tangential orientation impinge upon the mouth region which is to be examined (see FIG. 4B). Light beams which impinge tangentially upon the mouth region which is to be examined are not reflected upwardly and thus not into a camera which is disposed above the mouth, unless there is a defect in the mouth region. In order to achieve the desired degree of shielding, relatively complex light-guiding devices are required, e.g. an annular element having tangentially aligned holes or light-guiding plates. Moreover, a disadvantage of the known testing device is that it is not achieved to uniformly illuminate the sealing surface which is to be examined and light intensity on the whole is lost by virtue of the shielding arrangement. It is also not possible to achieve a tangential deflection simultaneously on both sides using the described light-guiding devices.

DE 36 86 847 T2 describes a testing device for detecting defects on a bottle neck which is provided with a screw thread. In the case of this known testing device, a tangential illumination of the region to be examined is also provided. The tangential illumination is achieved in turn by means of bores in an annular illumination device (see in particular FIGS. 3 and 4).

DE 39 40 693 C1 discloses a device for examining mouth regions, in which the principle of dark field illumination is applied. The light is transmitted in a radial direction on to a bottle mouth. Light is reflected into the camera only by the lips of the bottle mouth. There is no tangential illumination provided to obviate undesired reflections.

EP 0 657 732 A1 describes a device for optically examining a transparent mouth region, in which the region to be examined is observed in transmitted light by means of a substantially homogeneous light-radiating surface below said region to be examined. This testing method is not based upon the evaluation of reflections.

For the purpose of examining the mouth region, U.S. Pat. No. 4,731,649 describes an illumination device which is disposed substantially radially with respect to the mouth and which transmits light diffusely on to the region below the top edge of the mouth. A selective tangential irradiation is not provided.

In U.S. Pat. No. 2,868,061 there is provided a testing device for examining mouths of glass containers, in which a photomultiplier is used as a sensor. There is no provision to transmit light selectively in a tangential manner on to the mouth.

WO 90/04773 describes an optical system for recording an image for examining container mouths, wherein, however, no illumination device is used.

DE 31 47 086 A1 describes a device, in which light impinges tangentially upon a bottle mouth by means of a light conductor.

SUMMARY OF THE INVENTION

It is the object of the invention to provide a generic method of examining a container mouth which using simple means renders it possible to amplify contrast during the detection of defects in the mouth sealing surface. It is also the object of the invention to provide a generic device which is suitable for carrying out this method.

Light beams are transmitted by a light source, which is disposed generally above the mouth to be examined, from above on to the sealing surface. The light beams have a direction component which lies in the plane of the sealing surface and which is aligned tangentially with respect to the sealing surface or the lip of the mouth, respectively. For simplification, this is referred to here as the plane of the sealing surface, although the sealing surface comprises a curvature in the longitudinal direction of the mouth. Since the light beams are emitted from above, they also comprise a perpendicular direction component. Furthermore, the light beams in the sealing surface plane can also comprise a radial direction component which thus points towards the center or a longitudinal axis of the mouth. The light beams are predominantly reflected by the sealing surface. Most of the light beams are reflected in a lateral direction, so that the reflected light beams do not pass into a sensor which is disposed preferably above the mouth. However, if the light beams falling upon the sealing surface impinge upon a defect in the sealing surface, they are scattered in the form of scattered light beams, i.e. they are diffusely deflected, and at least some of the scattered light beams are detected by means of the sensor. It may be that the sensor also detects some of the reflected light beams. This can be a residual portion of reflected light beams which are directed upwardly as opposed to laterally. However, this can also relate to an intentionally generated intensity of light beams which are reflected in this manner, as will be explained hereinunder.

The tangential direction component is produced by virtue of the fact that in the beam path between the light source and the mouth there is disposed an optical deflecting element which is transparent at least to light of a certain wavelength and deflects impinging light beams of this wavelength accordingly. The deflecting element is thus produced from a correspondingly transparent material. Since the light beams which impinge upon the deflecting element can be diffused at least to a certain extent, there are generally also light beams which already have a tangential direction component even without the effect of the deflecting element. By virtue of the fact that the light beams are deflected merely by the deflecting element, no light intensity is lost, unless a specific light color is filtered out as described hereinunder. In accordance with the invention, the light beams are deflected by simple means.

It is preferably provided to split the light beams into two deflected beams which exit the deflecting element. This can be accomplished by using a corresponding prism element. In the case of light beams which comprise only a radial direction component in the sealing surface plane, it is thereby achieved that two beams which are deflected symmetrically with respect to a radius of the mouth impinge upon the sealing surface.

In particular, it can be provided that the deflecting element is symmetrical with respect to a longitudinal axis of a mouth to be examined and is disposed at least partially above the mouth, wherein over its length the deflecting element comprises in cross-section a larger circumference than the mouth. The light beams can be transmitted in an annular manner on to the optical deflecting element. In this manner, the sealing surface is illuminated uniformly.

It can be provided that all of the light beams which impinge upon the sealing surface must have previously passed the deflecting element. In this case, it possible to a large extent to prevent reflection rings from being produced. However, a relatively low reflection ring intensity can only be present due to the fact that by reason of the light beams impinging diffusely upon the deflecting element radial light beams are also present which are reflected to the sensor and are detected thereby as a reflection ring. However, it is advantageous in essence if the problem of superimposition of defect images by virtue of the reflection ring intensities can be obviated. On the other hand, reflection rings can, however, be desirable in order to position an evaluation region in an image which has been recorded by a camera which is used as a sensor. For this purpose, light beams can also be provided which are emitted in an annular manner on to the container mouth without these light beams having previously passed the deflecting element. These light beams should at least to a large extent be light beams which comprise only a radial direction component in the sealing surface plane. The reason for this is that, unless they impinge upon a defect, these beams are reflected by the sealing surface to the camera so that together they produce a reflection ring in the camera image.

Although suitable measures can be employed to adjust the intensity of these non-deflected light beams, these light beams will also produce an image of the flaw in the camera image if they are reflected by a flaw on the sealing surface. In order to avoid the above-described problem of superimposition of the defect images by virtue of the reflection rings, light of a different color can be used for the light beams which pass the deflecting element and for the light beams which do not pass the optical deflecting element and a color camera can be employed. In this case, the reflection rings comprise practically only an intensity in the color of the light beams which have not passed the deflecting element. In contrast, the defect scattered light intensities are composed of both colors. It is thus provided that the defects in the sealing surface are evaluated only in the color of those light beams which have passed the deflecting element, whereas the reflection rings are evaluated in the other color.

In particular, it can be provided that the deflecting element comprises a multiplicity of beam splitter prisms which are arranged in such a manner that an impinging light beam enters at the lateral surfaces of the prism. It is thus possible in a convenient manner to divide an incident light beam symmetrically into two partial beams which comprise a tangential direction component in the sealing surface plane. Preferably, the individual beam splitter prisms directly adjoin one another. The deflecting element is preferably in the shape of a hollow truncated cone, wherein it tapers in the direction of the sensor. The beam splitter prisms can be disposed on the peripheral surface or even on the inner surface of the hollow truncated cone.

The device comprises a light source and illumination means to illuminate the mouth by means of light beams which comprise a direction component impinging tangentially upon the sealing surface, i.e. have a tangential direction component in the sealing surface plane. Furthermore, the device comprises a sensor which is used to detect scattered light beams which are produced by the scattering of light beams at a defect in the sealing surface. By virtue of the fact that the illumination means comprise an optical deflecting element which is transparent at least for light of a certain wavelength and which is disposed in the beam path between the light source and the mouth and deflects impinging light beams of this wavelength to produce the tangential direction component, the advantages stated in relation to the method are achieved. The deflecting element comprises such a transparent material.

The deflecting element is preferably a hollow body which is at least substantially symmetrical in cross-section and which is disposed partially or completely above the mouth or the sealing surface and is open both at an upper end and a lower end. The sensor can be located above the upper end and a container which is to be examined can be positioned below the lower end of the hollow body. The hollow body can be a hollow cylinder.

In particular, the optical element can be a line splitter element. In this case, it is an element having a multiplicity of elongated beam splitter prisms which are disposed adjacent to one another. In particular, the beam splitter prisms can directly adjoin one another, so that all impinging light beams and light beams which have been let through are deflected.

Preferably, the deflecting element comprises the shape of a hollow truncated cone. An advantage of a hollow truncated cone form resides in the fact that light beams which are emitted perpendicularly by the light source impinge at a greater angle upon the deflecting element than in the case of a hollow cylinder shape and as a result undergo more extensive deflection.

The deflecting element can be a basic body having a line splitter film attached thereto. The line splitter film can be attached to an inner surface or an outer surface of the basic body. The deflecting element can also consist of a line splitter film which is folded together accordingly into the desired shape.

The illumination means are preferably designed such that the light beams impinge symmetrically or uniformly upon the mouth or sealing surface. This can be ensured in particular by virtue of the fact that in the beam path a diffuser disc is disposed between the light source and the deflecting element, which diffuser disc, in alignment with the container mouth and the sensor disposed over the diffuser disc, comprises an aperture for reflected light beams. The light source can uniformly transmit light beams on to the entire region of the diffuser disc which surrounds the aperture. The diffuser disc serves to scatter the light diffusely and the light passes partially on to the deflecting element. In this manner, the deflecting element is illuminated in the most uniform manner possible. As an alternative or in addition, a diffuse reflector can be disposed in the beam path between the light source and the mouth. This reflector is preferably symmetrical with respect to a longitudinal axis of the mouth and comprises in the center an aperture for light beams which are reflected by the sealing surface. The reflector is able to reflect light beams in particular on to the deflecting element. The reflector can comprise the shape of a hollow truncated cone which tapers in the direction of the mouth which is to be examined. This type of reflector renders it possible to utilize the light intensity produced by the light source in a particularly effective manner.

The deflecting element can naturally also be illuminated in a different manner, e.g. by means of an annular light source which directly emits light on to the deflecting element.

As described above with respect to the method, the illumination means can be designed in such a manner that light beams are also emitted in an annular manner on to the container mouth such that they produce reflection rings in the sensor or a camera. This is achieved by virtue of the fact that the light beams are not sent through the deflecting element. For example, a spaced interval can be provided between the deflecting element and the aperture of a diffuse reflector which is used, so that light beams can pass directly from the reflector on to the sealing surface which is to be examined. When these light beams comprise a radial direction component in the plane of the mouth, they produce the said reflection rings which can be used for positioning an evaluation region of the sensor or the camera.

In an advantageous manner, the illumination means are designed in such a manner that the light beams which pass the deflecting element have a different color than the light beams which do not pass the deflecting element. The sensor used is a color camera and, as described above, a single-color image in one color can be used in order to position the evaluation region by means of the reflection rings and a single-color image in the other color can be used in order to make defects in the sealing surface visible. Both images can be recorded simultaneously by the color camera but are separated from one another for the subsequent evaluation.

In order to produce the said different colored light beams, it is possible e.g. to produce the deflecting element from an optical material which lets through only light of a certain color. This can also be accomplished by attaching a color filter e.g. to the inner or outer side of a basic body. In addition, a color filter which lets through the desired other color can be provided between the deflecting element and the diffuse reflector. Alternatively, it is also possible to provide a spaced interval between the diffuser disc and an upper open end of the deflecting element, in order to produce the light beams impinging directly upon the sealing surface. A further way of producing these beams is to provide a free spaced interval between a lower and an upper part of the deflecting element. In the case of these further embodiments, the second color filter can be used in each case in the spaced interval regions.

Furthermore, the respective light of a certain color can also be produced by virtue of the fact that two light sources are used which each emit the desired colored light. In order to ensure that only the light of the desired color passes through the deflecting element, the deflecting element can be separated from the light of the other color by means of a corresponding light shield.

BRIEF DESCRIPTION OF THE DRAWINGS

The invention will be explained in detail hereinunder with reference to exemplified embodiments, wherein reference is made to the Figures, in which.

In all of the Figures, like features are designated by like reference numerals.

DETAILED DESCRIPTION OF THE EMBODIMENTS

Figure 1:
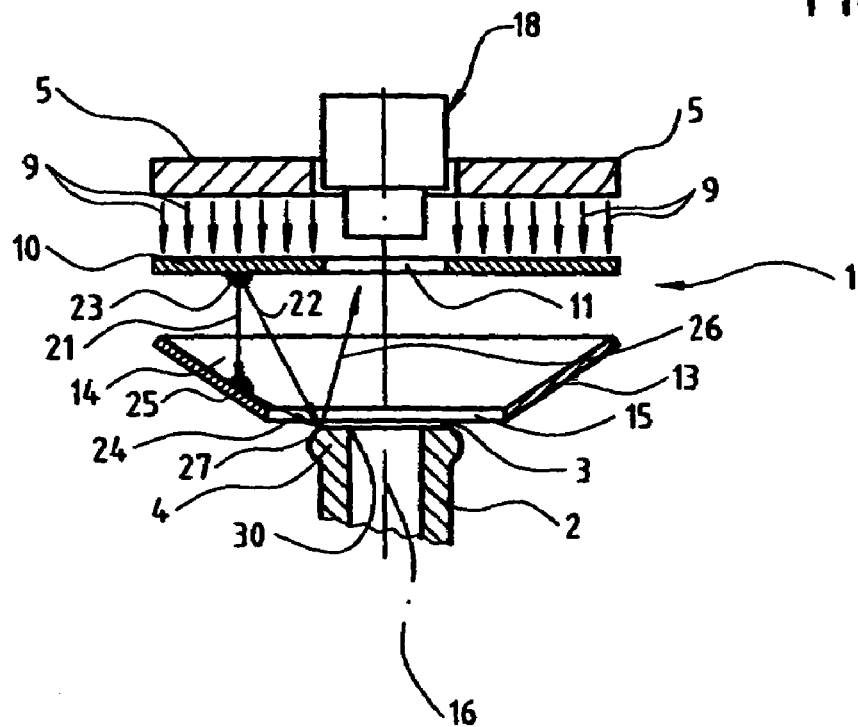
FIG. 1 shows a schematic sectional view of a testing device which is know in practice.
Figure 2:
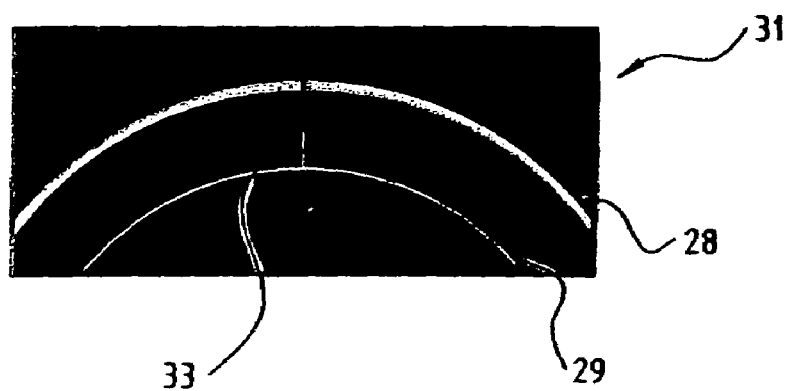
FIG. 2 shows a section of a schematic basic illustration of an image recorded by a camera of the testing device of FIG. 1.
Figure 3A:
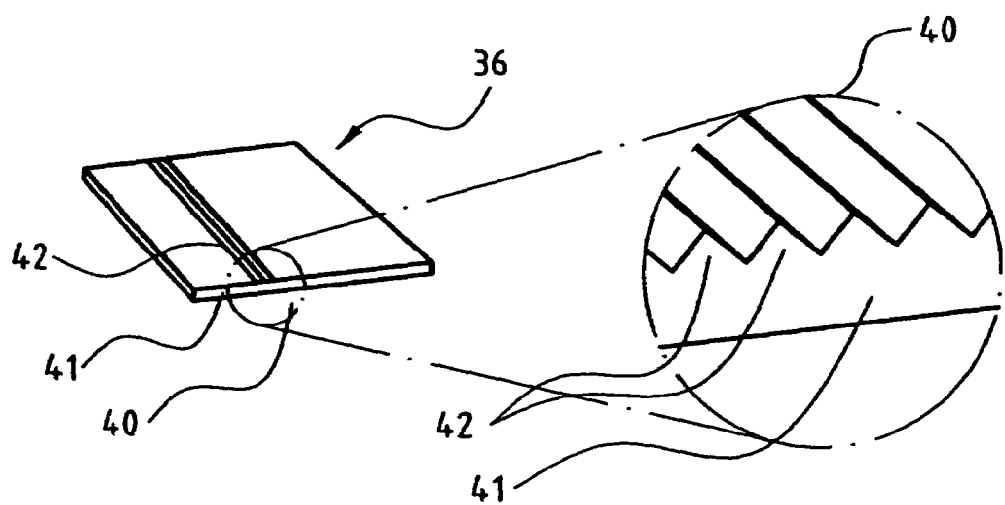
FIG. 3a shows an enlarged schematic illustration of a section of a line splitter film which is known per se.
Figure 3B:
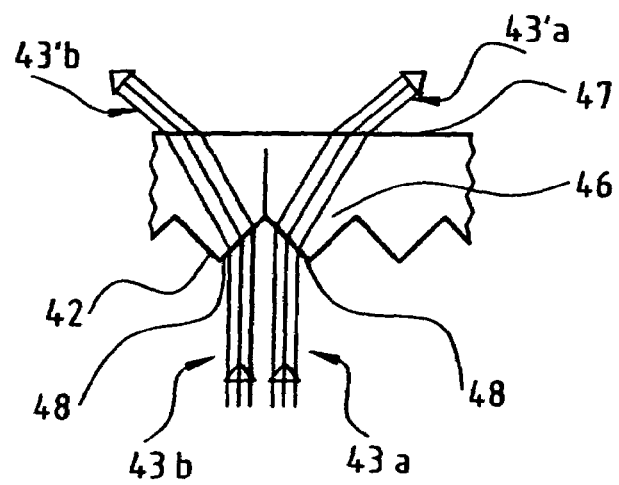
FIG. 3b shows schematically the principle of the deflection of light beams through a prism strip of a line splitter film.

FIG. 3a illustrates a line splitter film 36, as can be used as a component of an optical deflecting element 38 or 39 described hereinunder. As shown in particular in an enlarged section 40, the line splitter film 36 comprises a planar base 41. One side of the base 41 is occupied completely by parallel prism strips 42 (not all of which are illustrated) which directly adjoin one another. The prism strips 42 are elongated prisms consisting of translucent material. As shown in FIG. 3b, light beams which are aligned perpendicularly with a smooth underside 47 of the line splitter film 36 and impinge upon lateral surfaces 48 of the prism strips 42 are broken. The broken light beams pass through the prism base 46 to the smooth underside 47 of the line splitter film 36 and are broken once again at this location. By reason of the effect of the corresponding prism strip 42 the light beams 43a produce the light beams 43'a and the light beams 43b produce the light beams 43'b. In FIG. 3b, light beams 43a and 43b are illustrated separately to illustrate the deflection principle, but they can be considered to form a light beam 43 together (see FIG. 4).

Figure 4:
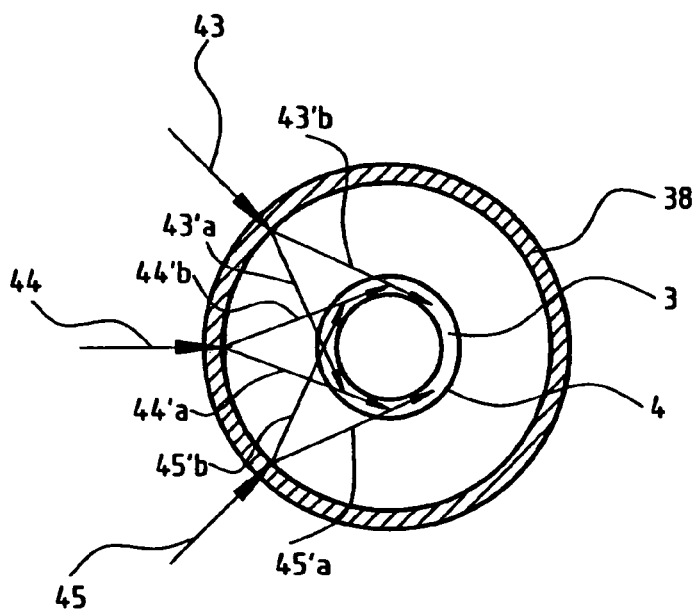
FIG. 4 shows schematically the principle of beam deflection through the optical deflecting element forming the basis of the invention.
Figure 5:
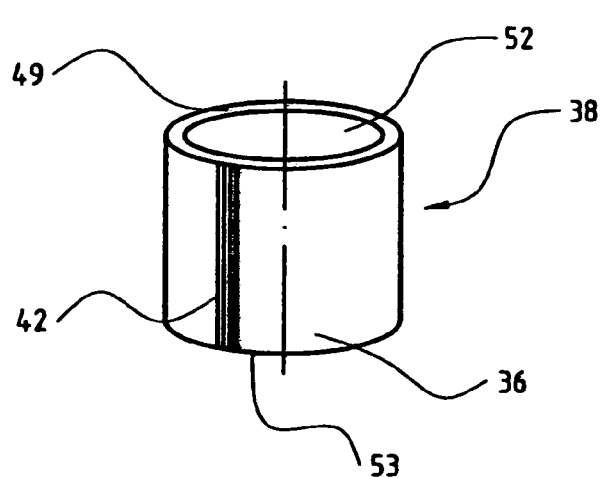
FIG. 5 shows a perspective view of a first embodiment of an optical deflecting element in accordance with the invention.

A deflection of light beams as produced in this manner is utilized in accordance with the invention, in order to transmit light beams tangentially to a sealing surface 3 of a container mouth 4 which is to be examined. FIG. 4 illustrates this principle. Light beams 43, 44 and 45 comprise merely a radial direction component in the sealing surface plane which is identical to the plane of the drawing. The light beams 43, 44 and 45 impinge upon an optical deflecting element 38 which is illustrated in FIG. 5. The deflecting element 38 comprises a transparent, hollow-cylindrical basic body 49. Attached to the basic body 49 is a line splitter film 36 such that it covers the entire outer surface of the deflecting element 38 and the respective base 46 of the paraxial prism strips 42 faces inwards. As explained above, the light beams 43, 44 and 45 are divided by the prism strips 42 in each case into two light beams 43'a, 43'b, 44'a, 44'b, 45'a and 45'b which in the sealing surface plane comprise both a tangential component and a radial component, not illustrated separately. Since the tangential light beams 43'a, 43'b, 44'a, 44'b, 45'a and 45'b pass tangentially over the mouth, they are reflected by the sealing surface 3 in a lateral manner and not upwardly out of the sealing surface plane, as explained in detail hereinunder.

Figure 6:
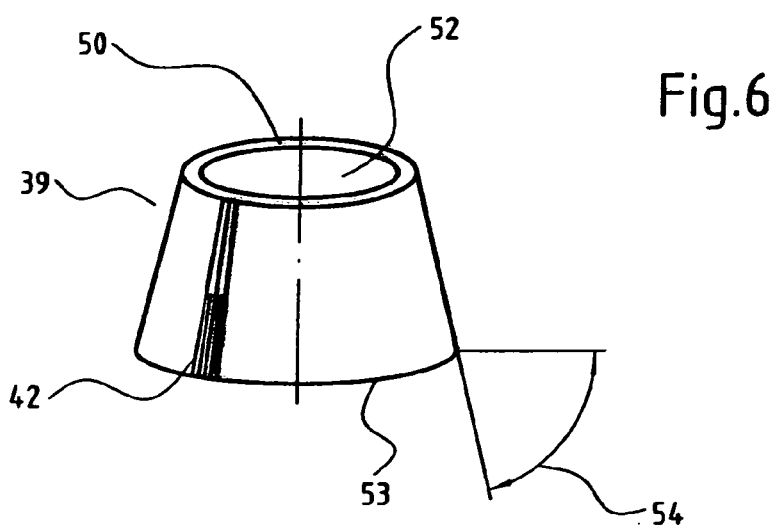
FIG. 6 shows a perspective view of a second embodiment of an optical deflecting element in accordance with the invention.

FIG. 6 illustrates another optical deflecting element 39 which differs from the deflecting element 38 by virtue of the fact that it comprises a transparent, hollow truncated cone-shaped basic body 50. The deflecting elements 38 and 39 each comprise an upper open end 52 and a lower open end 53. In particular, the angle, as designated by the reference numeral 54 in FIG. 6, between the peripheral surface of the deflecting element 39 and the horizontal can amount to 30° to 80°.

Figure 7:
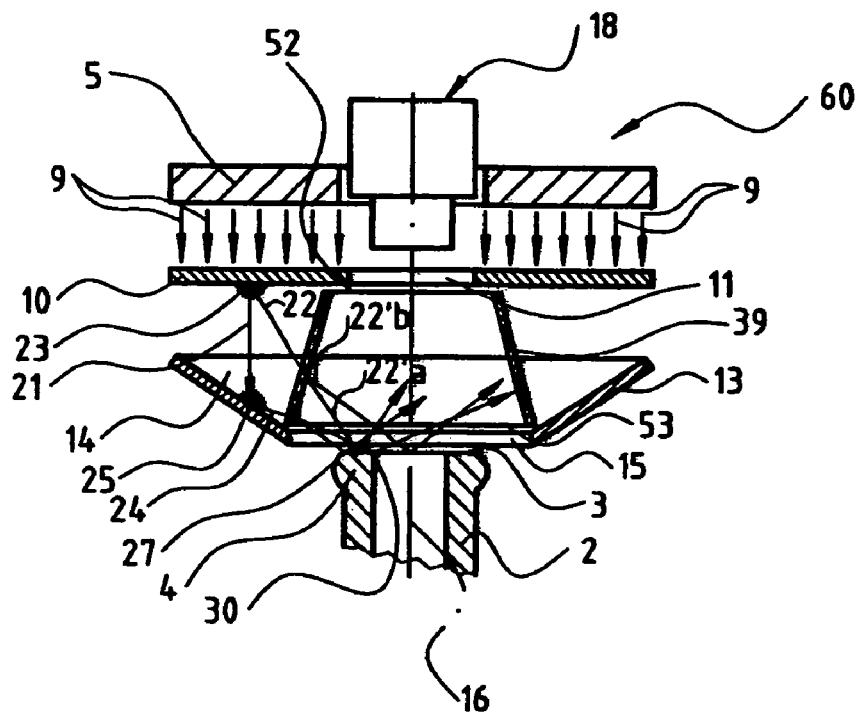
FIG. 7 shows a schematic sectional view of a first embodiment of a testing device in accordance with the invention and of a bottle mouth.

The testing device in accordance with the invention as shown in FIG. 7 is designated by the reference numeral 60. In comparison with the known testing device 1, the testing device 60 additionally comprises an optical deflecting element 39 which is disposed in a paraxial manner between the mouth 4 and the camera 18. The deflecting element 39 is mounted with its lower open end 53 without a spaced interval above the lower orifice 15 of the diffuse reflector 13. The upper open end 52 of the deflecting element 39 is located directly below the orifice 11 of the diffuser disc 10.

In this manner, the light beams which leave the diffuser disc 10 can impinge either directly upon the deflecting element 39 which is the case e.g. for the light beam 22, or can impinge upon the inner surface 14 of the reflector 13, as is the case for the light beam 21. The light beam 22 is divided or deflected into two beams 22'a and 22'b by the deflecting element 39, as described above. The two deflected light beams 22'a and 22'b comprise a tangential direction component in the plane of the sealing surface 3 and as they impinge upon the sealing surface 3 they are not reflected upwardly into the paraxial camera 18 but rather are reflected laterally. The greater the deflection of the light beams which impinge upon the deflecting element 39, the lower the intensity of reflected light beams which are directed upwardly into the camera 18. Greater deflection can be achieved by virtue of the fact that the angle 54 of the deflecting element 39 is made smaller.

The light beam 24 which is produced by reflection on the reflector 13 likewise impinges upon the deflecting element 39 and, like the light beam 22, it is divided or deflected into two light beams, illustrated but not referenced. In turn, these light beams also comprise a tangential direction component and are not reflected into the camera 18 as they impinge upon the sealing surface 3.

The deflecting element 38 could also be utilized instead of the deflecting element 39. However, in this case the light from the inner edge of the diffuser disc 10 would impinge in an extremely flat manner upon the peripheral surface of the deflecting element 38 and would only be split up at a very small angle. This could be counteracted by virtue of the fact that the diameter of the orifice 11 of the diffuser disc 10 would be made larger and accordingly the irradiated surface of the diffuser disc 10 would be adapted.

Figure 8:
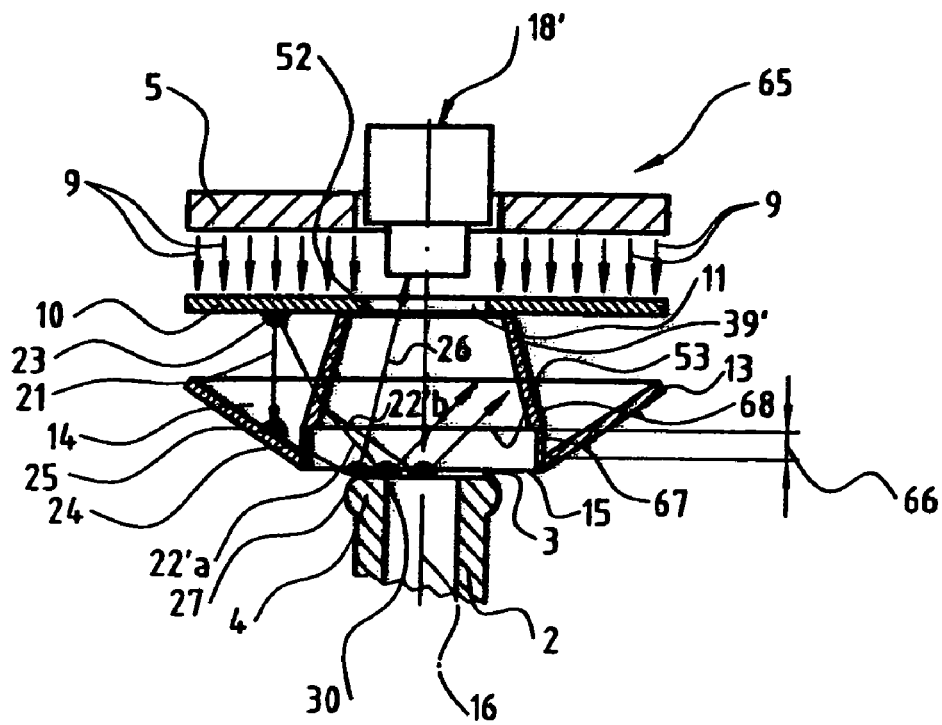
FIG. 8 shows a schematic sectional view of a second embodiment of a testing device in accordance with the invention and of a bottle mouth.

The testing device in accordance with the invention as shown in FIG. 8 is designated by the reference numeral 65. The testing device 65 differs from the testing device 60 by virtue of the fact that it is intended to produce reflection rings in order to use them to position an evaluation region of a color camera 18'. The reflection rings are produced by virtue of the fact that a deflecting element 39' is disposed at a spaced interval 66 above the reflector 13. Disposed in the intermediate space 66 is a hollow-cylindrical green color filter 67. Light beams, such as e.g. light beam 24, which pass by underneath the deflecting element 39' and through the color filter 67 on to the sealing surface 3 thus generate green reflection rings in the color camera 18'.

The basic body of the deflecting element 39' is a red color filter 68. Light beams which, like the light beam 22, impinge upon the deflecting element 39' thus become red light. As described above, the light beams of this red light do not contribute to the reflection rings but rather only pass into the camera 18' if they are diffusely scattered into the camera 18' at defects on the sealing surface 3. Therefore, the evaluation region is positioned by means of the reflection rings in a green channel of the image and the evaluation of possible defects is performed in a red channel of the image. Of course, it is also possible to use other colors or other color filters. The advantage of using different colors resides in the fact that the intensity of the light which is emitted by the light source 5 can be increased without any superimposition fading of defect images occurring in the generated camera image as a result of the reflection rings. The sensitivity of the color camera 18' to red light can be arbitrarily greater than the sensitivity to green light. This is very advantageous because the reliability and accuracy of the detection of defects increases with the light power.

Figure 9:
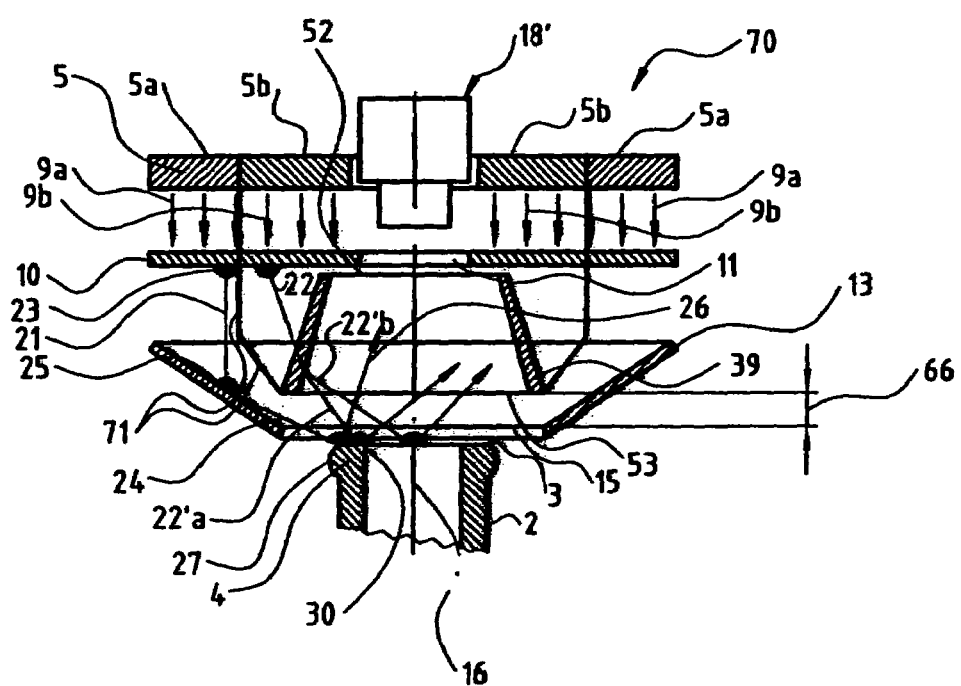
FIG. 9 shows a schematic sectional view of a third embodiment of a testing device in accordance with the invention and of a bottle mouth.

The testing device in accordance with the invention as shown in FIG. 9 is designated by the reference numeral 70. The testing device 70 differs from the testing device 65 by virtue of the fact that light of a different color is produced by two different light sources 5a and 5b which are components of a light source 5. The light source 5a emits green light beams 9a and the light source 5b emits red light beams 9b. A shield 71 serves to ensure that light beams which originate from the light source 5a do not impinge upon the deflecting element 39 and on the other hand no light beams which originate from the light source 5b pass by underneath the deflecting element 39 through the intermediate space 66 and on to the sealing surface 3 and thus contribute to reflection rings in an image recorded by the color camera 18'. No filters are required in the testing device 70. The light sources 5a and 5b can each comprise e.g. a set of green and red light-emitting diodes respectively. The advantages described with respect to the testing device 65 are also achieved in the testing device 70.

The invention claimed is:

1. A method of detecting defects in a sealing surface of a container, said method comprising:
   providing a sensor;
   providing a light source;
   providing an optical deflecting element positioned between said light source and said sealing surface, said optical deflecting element being transparent to at least light of a certain wavelength;
   projecting a plurality of first light beams onto said optical deflecting element;
   deflecting said first light beams to produce a direction component tangential to said sealing surface in the plane of said sealing surface; and
   detecting, with said sensor, at least some of said tangential components impinging on said sealing surface after having been scattered by said defects.

2. A method according to claim 1, further comprising dividing each of said first light beams into two light beams using said optical deflecting element.

3. A method according to claim 2, wherein dividing each of said light beams comprises passing said light beams through a multiplicity of beam splitter prisms which said optical deflecting element comprises.

4. A method according to claim 1, wherein said optical deflecting element is positioned symmetrically about an axis through the center of said sealing surface and has a circumference greater than that of said sealing surface, said method further comprising projecting said first light beams onto said optical deflecting surface in the form of an annulus.

5. A method according to claim 1, wherein said sensor comprises a camera, said method further comprising:
   projecting a plurality of second light beams onto said sealing surface, said second light beams being radially oriented relatively to said sealing surface in the plane of said sealing surface;
   producing reflection rings from said second light beams reflected from said sealing surface; and
   using said reflection rings to position an evaluation region of an image recorded using said camera.

6. A method according to claim 5, wherein said camera is a color camera, said method further comprising:
   projecting said first light beams in a first color, said defects scattering said first light beams in said first color;
   projecting said second light beams in a second color different from said first color, said reflection rings being in said second color; and
   detecting, with said camera, said defects in said first color and said reflection rings in said second color.

7. A method according to claim 1, wherein said optical deflecting element is formed as a hollow truncated cone positioned between said sealing surface and said sensor, said cone tapering in a direction toward said sensor.

8. A device for detecting defects in a sealing surface of a container, said device comprising:
   a sensor positioned to receive light scattered from said sealing surface;
   a first light source positioned to illuminate said sealing surface and emitting a plurality of light beams; and
   an optical deflecting element positioned between said first light source and said sealing surface, said deflecting element being transparent to at least light of a certain wavelength, said deflecting element deflecting a first group of said light beams with a component in a direction tangential to said sealing surface in the plane of said sealing surface, at least some of said first group of said light beams impinging with said component tangentially on said sealing surface, defects in said sealing surface scattering a portion of said first group of said light beams, said sensor detecting at least some of said portion of said first group of said light beams scattered by said defects.

9. A device according to claim 8, wherein said optical deflecting element comprises a hollow body having a symmetric cross-section, said body being open at both ends.

10. A device according to claim 9, wherein said optical deflecting element comprises a hollow cylinder.

11. A device according to claim 9, wherein said optical deflecting element comprises a hollow truncated cone.

12. A device according to claim 8, wherein said optical deflecting element comprises a multiplicity of beam splitter prisms.

13. A device according to claim 12, wherein said optical deflecting element comprises a beam splitter element.

14. A device according to claim 13, wherein said beam splitter element comprises a body having a surface on which a film comprising said beam splitter element is attached.

15. A device according to claim 8, further comprising a diffuser disk positioned between said first light source and said optical deflecting element, said diffuser disk having an orifice aligned with said sensor.

16. A device according to claim 8, further comprising a diffuse reflector positioned between said first light source and said sealing surface, said reflector being symmetric about an axis through the center of said sealing surface and having an orifice aligned with said sealing surface permitting light reflected from said sealing surface to pass through.

17. A device according to claim 16, wherein said first light source is designed to permit radial direction components of said light beams, reflected directly from said diffuse reflector and said direction components being in the plane of the sealing surface to impinge on said sealing surface without first passing through said optical deflecting element and reflect from said sealing surface to project reflection rings to said sensor.

18. A device according to claim 16, wherein said first light source is designed to permit radial direction components of said light beams, said direction components being in the plane of the sealing surface to impinge on said sealing surface without first passing through said optical deflecting element and reflect from said sealing surface to project reflection rings to said sensor and said optical deflecting element is disposed at a spaced interval above said orifice of said diffuse deflector such that light beams pass directly from said diffuse reflector on to said sealing surface.

19. A device according to claim 8, wherein said first light source is designed to permit radial direction components of said light beams, said direction components being in the plane of the sealing surface to impinge on said sealing surface without first passing through said optical deflecting element and reflect from said sealing surface to project reflection rings to said sensor.

20. A device according to claim 19, wherein said sensor is a color camera, and wherein said light source is designed such that radial components of said light beams which impinge on said sealing surface without passing through said optical deflecting element comprise a second color different from light beams, having a first color, which pass through said optical deflecting element, said reflecting rings being reflected to said camera in said second color, said defects in said sealing surface being detected by said camera in said first color.

21. A device according to claim 20, further comprising a first color filter inserted between said optical deflecting element and a diffuse reflector positioned between said first light source and said sealing surface, said diffuse reflector being spaced apart from said optical deflecting element, and, said optical deflecting element comprising a second color filter.

22. A device according to claim 20, wherein said light source emits light at a first color, said device further comprising:
 a second light source emitting light at a second color; and
 a light shield disposed in a beam path to prevent light which is intended to pass through said optical deflecting element from mixing with light beams not passing through said optical deflecting element.

\* \* \* \* \*